US00PP32830P3

(12) United States Plant Patent
Yoshida et al.

(10) Patent No.: US PP32,830 P3
(45) Date of Patent: Feb. 23, 2021

(54) ***CAMELLIA SINENSIS* (L.) KUNTZE PLANT NAMED 'KIYOKA'**

(50) Latin Name: ***Camellia sinensis* (L.) Kuntze**
Varietal Denomination: Kiyoka

(71) Applicant: National Agriculture and Food Research Organization, Ibaraki (JP)

(72) Inventors: Katsuyuki Yoshida, Ibaraki (JP); Akiko Ogino, Ibaraki (JP); Atsushi Nesumi, Ibaraki (JP); Tetsuji Saba, Ibaraki (JP); Junichi Tanaka, Ibaraki (JP); Fumiya Taniguchi, Ibaraki (JP); Shuya Yamashita, Ibaraki (JP); Hiroshi Yorozuya, Ibaraki (JP); Akiko Matsunaga, Ibaraki (JP); Yoshiyuki Takeda, Ibaraki (JP); Tsuyoshi Okamoto, Ibaraki (JP); Hitoshi Yoshitomi, Ibaraki (JP)

(73) Assignee: National Agriculture and Food Research Organization, Ibaraki (JP)

( * ) Notice: Subject to any disclaimer, the term of this patent is extended or adjusted under 35 U.S.C. 154(b) by 0 days.

(21) Appl. No.: 16/602,869

(22) Filed: Dec. 12, 2019

(65) Prior Publication Data

US 2020/0196503 P1 Jun. 18, 2020

(30) Foreign Application Priority Data

Dec. 14, 2018 (JP) ..... PBR 33551

(51) Int. Cl.
*A01H 5/12* (2018.01)
*A01H 6/00* (2018.01)

(52) U.S. Cl.
USPC ..... Plt./243
CPC ..... *A01H 6/00* (2018.05); *A01H 5/12* (2013.01)

(58) Field of Classification Search
USPC ..... Plt./243
CPC ... A01H 5/12; A01H 5/02; A01H 5/00; A01H 6/00; A01H 6/14
See application file for complete search history.

(56) References Cited

PUBLICATIONS

International *Camellia* Society for *Camellia* Register for K, retrieved on Jun. 11, 2020, retrieved from the Internet at https://internationalcamellia.org/camellia-register-pdf-downloads, cover page and p. 88. (Year: 2020).*

* cited by examiner

*Primary Examiner* — June Hwu
(74) *Attorney, Agent, or Firm* — Mintz, Levin, Cohn, Ferris, Glovsky and Popeo, P.C.

(57) ABSTRACT

'Kiyoka' is a new variety of tea plant bred by crossbreeding FYZ-41 ('Yabukita' x 'Shizuinzatsu 131'), a hybrid, as the female parent and 'Saemidori' as the male parent. The steamed leaves and leaf buds of 'Kiyoka' have a distinctive floral aroma, and excellent taste.

4 Drawing Sheets

Plant name and variety denomination:

Latin name of the genus and species of the plant claimed: *Camellia sinensis* (L.) Kuntze. The claimed plant is a hybridization of different varieties.

Common names of the claimed plant's species: Tea plant.

Variety denomination: 'Kiyoka'.

BACKGROUND

*Camellia sinensis* (L.) Kuntze, commonly called tea plant or tea shrub, is an evergreen shrub or small tree whose leaves and leaf buds are used to produce tea. *Camellia sinensis* is mainly cultivated in tropical and subtropical climates. *Camellia sinensis* is native to East Asia, the Indian Subcontinent, and Southeast Asia, however it is currently cultivated across the world in tropical and subtropical regions.

BRIEF SUMMARY

'Kiyoka' is a new variety of *Camellia sinensis* (L.) Kuntze bred by crossbreeding FYZ-41 ('Yabukita' x 'Shizuinzatsu 131'), a hybrid, as the female parent and 'Saemidori' as the male parent. 'Kiyoka' is propagated by grafts or cuttings.

The plant may be used, e.g., for cultivation of tea leaves and leaf buds for consumption. 'Kiyoka' has been asexually reproduced in Kagoshima prefecture, Japan. 'Kiyoka' is propagated by cutting. Cutting is a method in which a young shoot is adjusted to a cutting having one leaf or two leaves, and the cutting is then inserted into soil, or the like, so as to take root.

Approximately 75% of Japan's tea fields are used for cultivating 'Yabukita'. An adverse effect of such singular cultivation is that Japanese tea lacks diversity of aroma and flavor. Currently, the needs of commercial users and consumers of tea are diversifying, and there is a need for new tea varieties which have their own distinctive aroma and flavor. To date, the tea varieties 'Sofu' and 'Fuji Kaori' (which are crossbreeds between 'Yabukita' and 'Assam' variant progeny lines) have been bred as varieties having a distinctive aroma. However, when such teas are used as sencha (a type of Japanese green tea), while they do have an excellent oriental-orchid-like floral fragrance, they also often have an astringent flavor. There has been development of new techniques for withering plucked fresh leaves in a manner that enhances aroma, by utilizing low-temperature moisture-removal withering or new artificial withering devices. Unfortunately, such techniques result in a tea whose color of liquor differs from that of sencha and is closer to that of semi-fermented tea.

'Kiyoka' is a variety obtained by selecting individuals from progeny of a crossbreed between (i) FYZ-41 (seed parent), which is an Assam variant crossbreed progeny having a floral fragrance, and (ii) 'Saemidori', which is a high-quality variety having strong umami. 'Kiyoka' is characterized in that (i) it has a clean and distinctive floral fragrance like that of an oriental orchid, (ii) its color of liquor is greenish, and (iii) it has a flavor exhibiting umami. 'Kiyoka' is early budding and thus limited in terms of cultivation region, and its yield is less than that of 'Saemidori'. However, 'Kiyoka' presents the possibility of development of new products which utilize its new characteristic aroma and flavor.

DETAILED BOTANICAL DESCRIPTION OF THE PLANT

Figure 1:
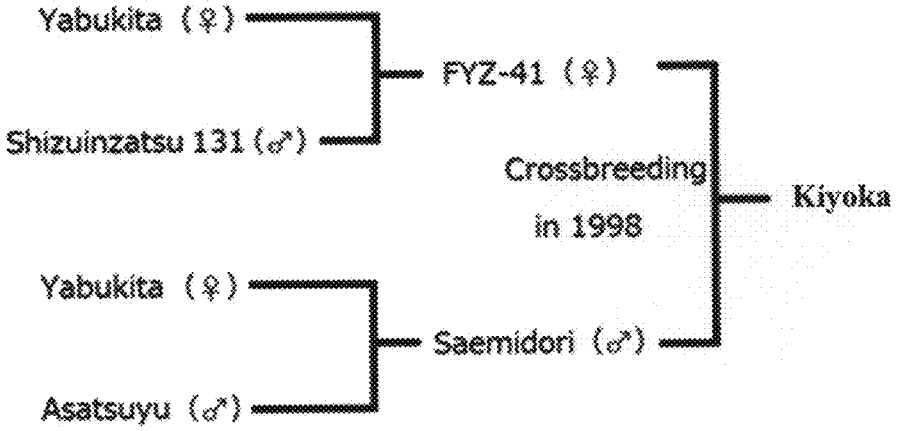
FIG. 1 is a breeding pedigree chart for 'Kiyoka'.
Figure 2:
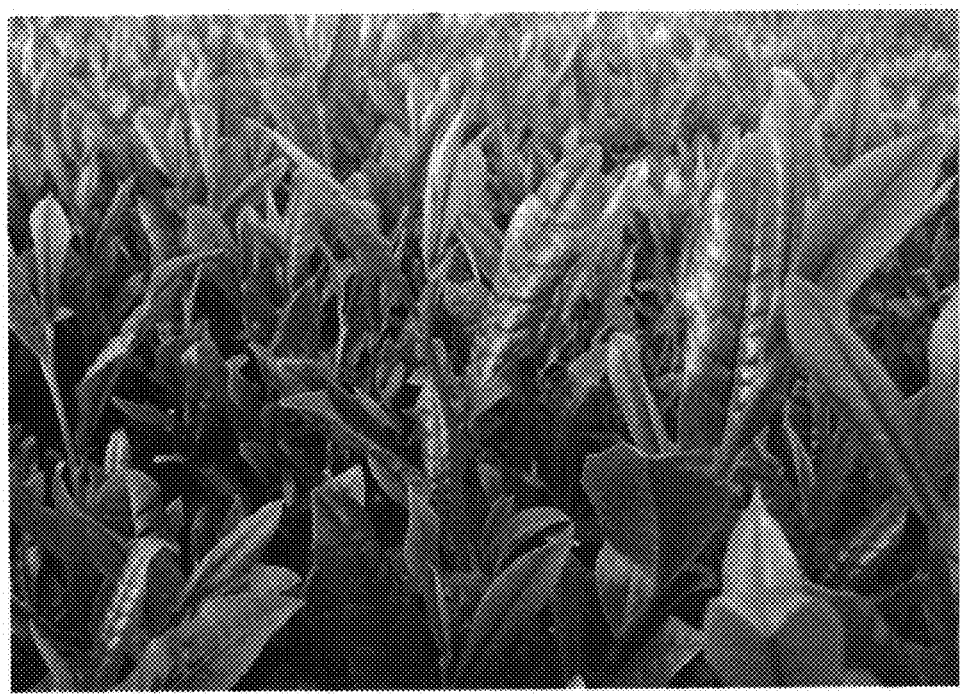
FIG. 2 is a photograph of 'Kiyoka' first flush, young shoots.
Figure 3:
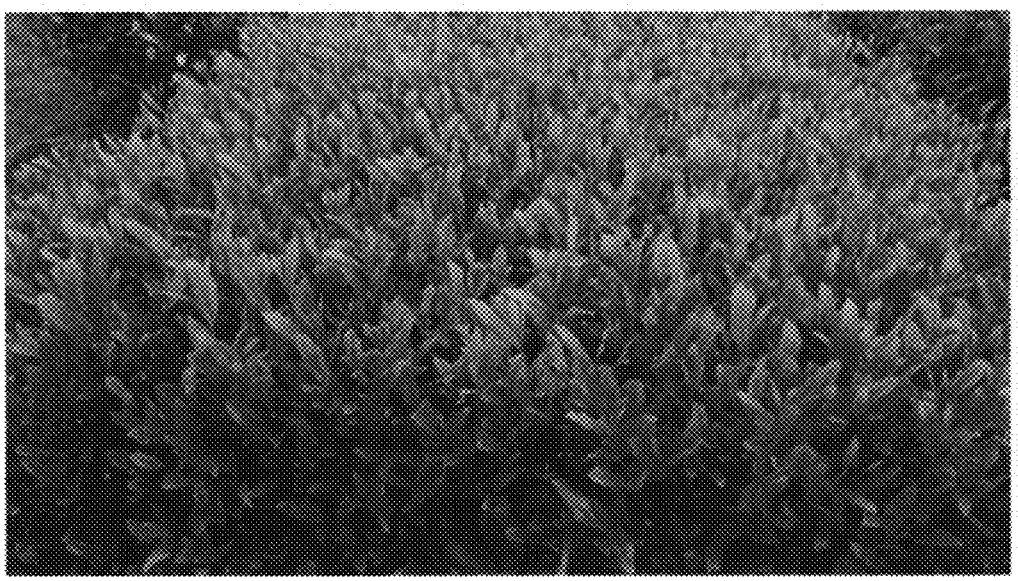
FIG. 3 is a photograph of the state of 'Kiyoka' plants at time of first flush.
Figure 4:
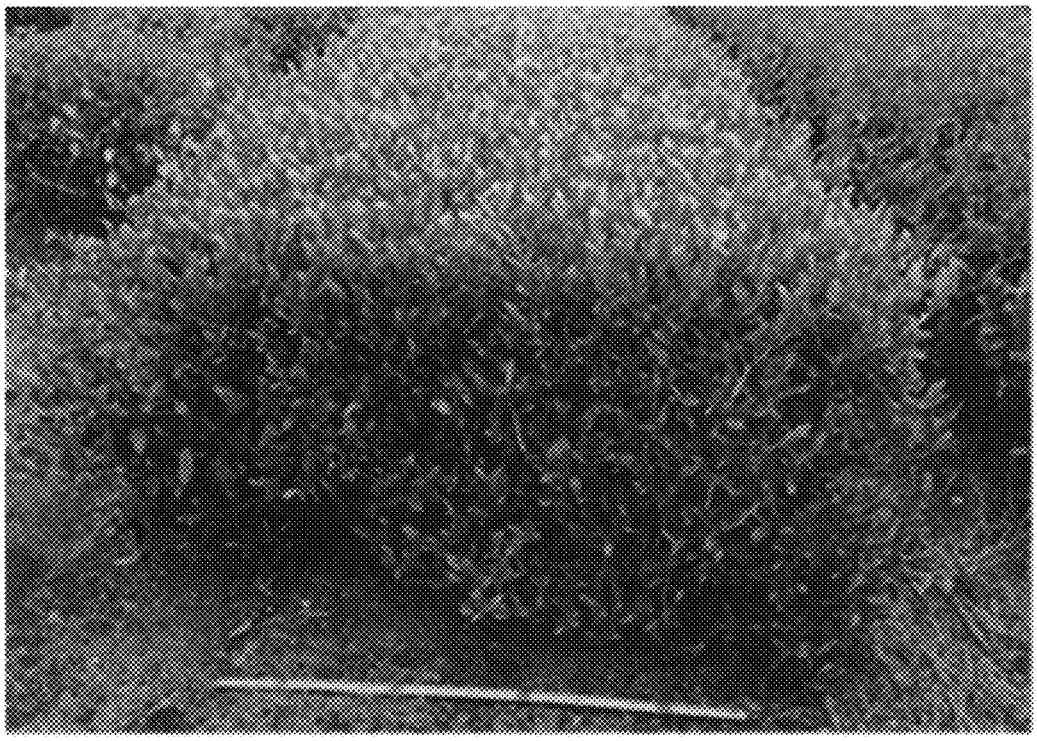
FIG. 4 is a photograph of the state of 'Kiyoka' plants in the cultivation field at the time of plucking. Ruler shown is 1 meter.
Figure 5:
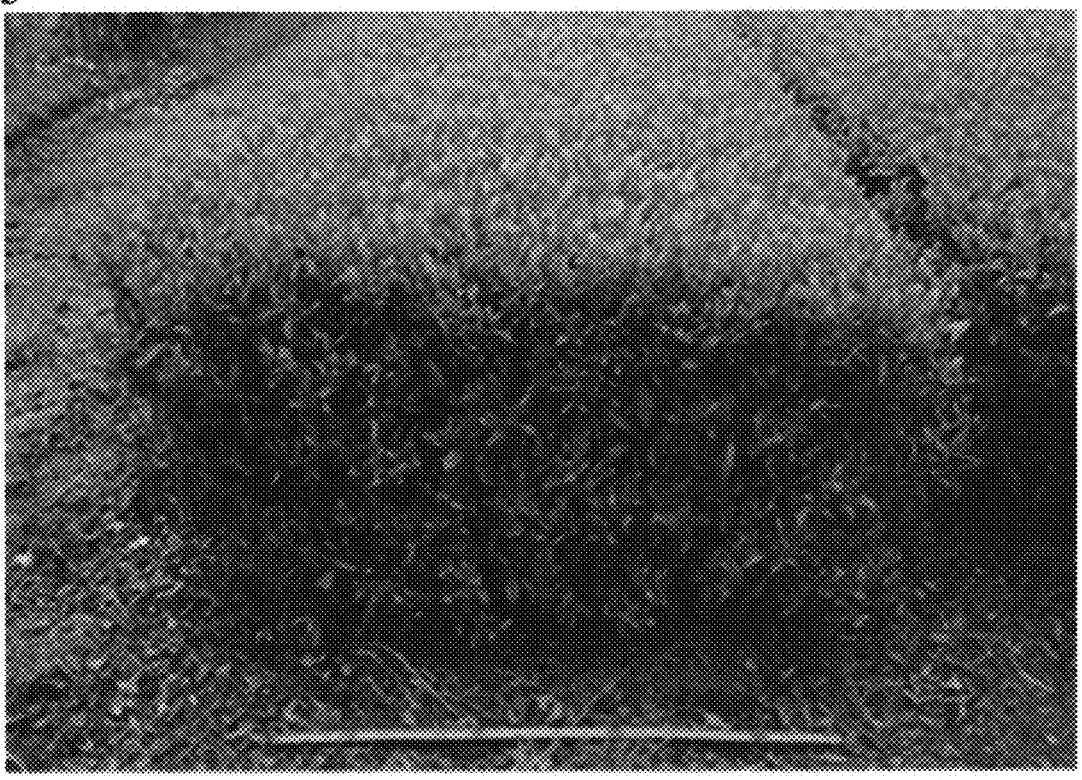
FIG. 5 is a photograph of the state of parent variety 'Saemidori' plants in the cultivation field at the time of plucking. Ruler shown is 1 meter.
Figure 6:
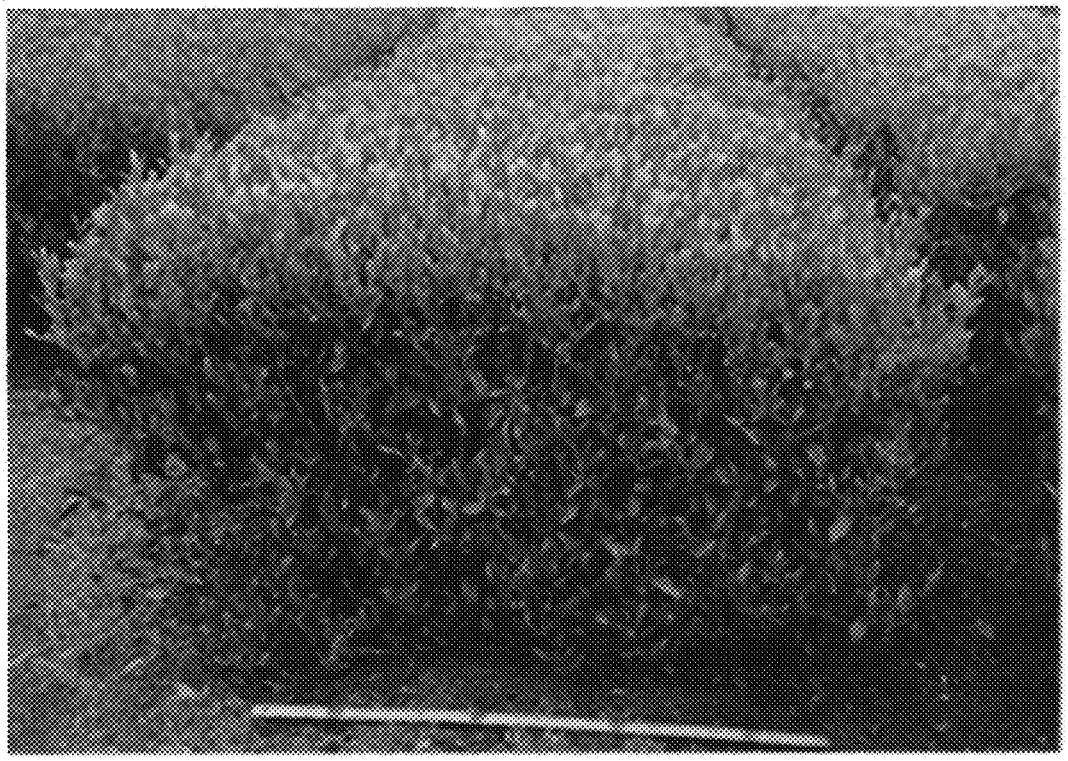
FIG. 6 is a photograph of the state of grandparent variety 'Yabukita' plants in the cultivation field at the time of plucking. Ruler shown is 1 meter.
Figure 7:
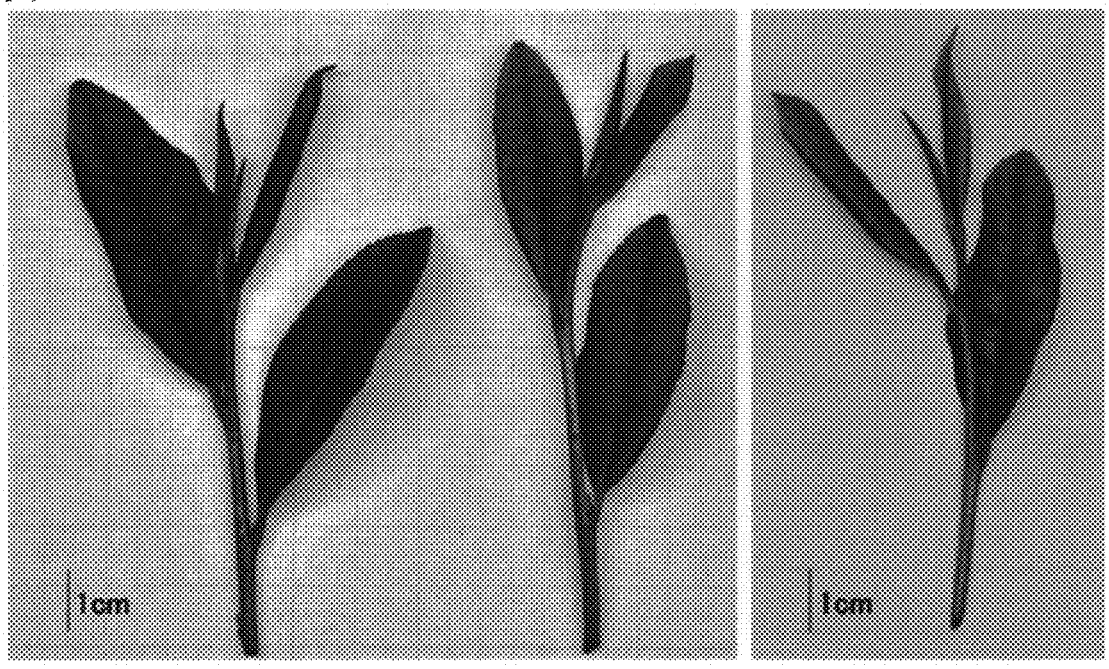
FIG. 7 is a photograph of the shape of young shoots at plucking (first flush) of 'Kiyoka' (left), 'Saemidori' (center), and 'Yabukita' (right).
Figure 8:
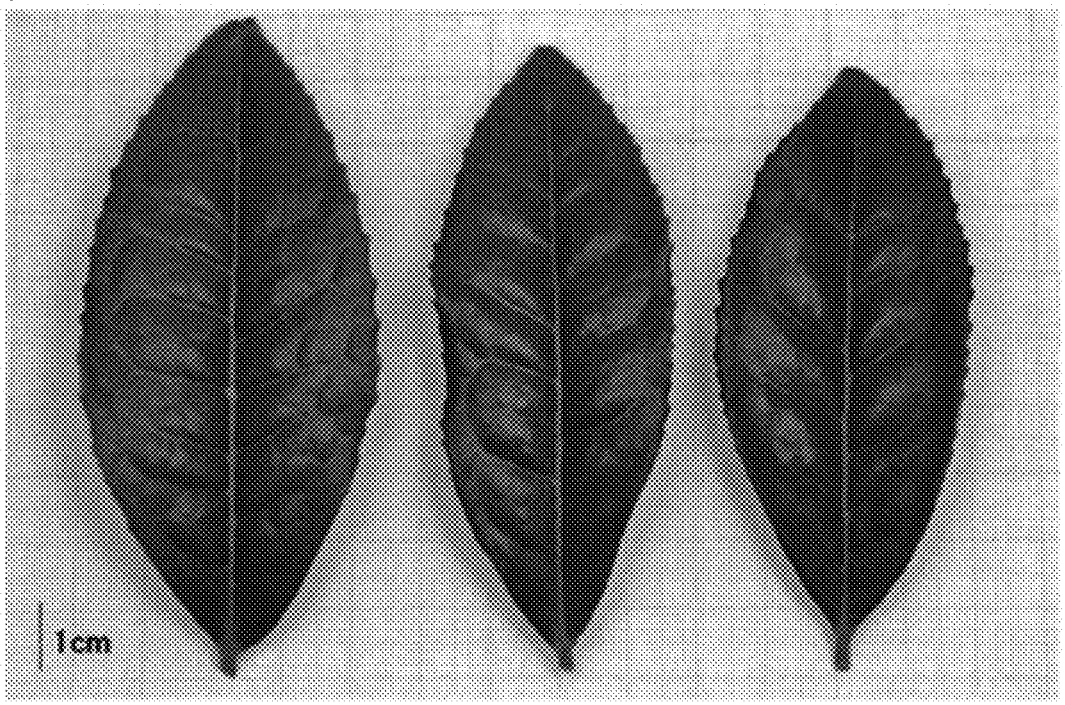
FIG. 8 is a photograph of the shape of young leaves from water sprout at plucking (first flush) for 'Kiyoka' (left), 'Yabukita' (center), and 'Saemidori' (right).

Variety: 'Kiyoka'.

Species of the plant claimed: *Camellia sinensis* (L.) Kuntze.

Common names of the claimed plant's species include: tea plant or tea shrub.

Characteristics of 'Kiyoka' provided herein were observed when the plant was cultivated in Japan.

Properties and characteristics of 'Kiyoka', compared to the parent varieties, are described in Tables 1 and 2 below.

TABLE 1

Properties and characteristics of 'Kiyoka' clearly distinguishable from similar varieties.

| Denomination of Similar Variety | Description of Characteristics | State of Expression in Similar Variety | State of Expression in 'Kiyoka' |
|---|---|---|---|
| Yabukita | Plant: vigor | Weak to medium | Medium to strong |

TABLE 1-continued

Properties and characteristics of 'Kiyoka' clearly distinguishable from similar varieties.

| Denomination of Similar Variety | Description of Characteristics | State of Expression in Similar Variety | State of Expression in 'Kiyoka' |
|---|---|---|---|
| Saemidori | Plant: vigor | Weak to medium | Medium to strong |
| Yabukita | Plant: growth habit | Upright to semi upright | Semi upright to spreading |
| Yabukita | Time of sprouting | Medium | Early |
| Yabukita | Young shoot: beginning of "one and a bud" stage | Medium time of | Early |
| Yabukita | Time of plucking | Medium | Early |
| Yabukita | Leaf blade: intensity of green color | Medium | Light |
| Saemidori | Leaf blade: intensity of green color | Medium | Light |
| Yabukita | Fermentation ability | Weak | Medium |
| Saemidori | Fermentation ability | Weak | Medium |

TABLE 2

Table of Characteristics: Kiyoka (data from two years; in cases where characteristic is identical in second year, per-year results are not shown).

| Characteristics | Characteristics | | State/score of expression in candidate variety | | |
|---|---|---|---|---|---|
| No. | Characteristic | note | state | score | data |
| 1 | Vigor | Plant | Medium to strong | 6 | |
| 2 | Type | Plant | Shrub | 1 | |
| 3 | Growth habit | Plant | Semi upright to spreading | 4 | |
| 4 | Density of branches | Plant | Medium | 5 | |
| 5 | Branch zigzagging | Plant | Absent | 1 | |
| 6 | Time of sprouting | 70% of the plants show sprouts | Early | 3 | Mar. 12, 2016 Mar. 23, 2017 |
| 7 | Time of beginning | One and two bud stage of young shoot | Early | 3 | Mar. 23, 2016 Apr. 3, 2017 |
| 8 | Color of the third leaf | Three and a bud stage of young shoot | Medium green | 4 | 140A |
| 9 | Pubescence of bud | Young shoot | present | 9 | |
| 10 | Density of pubescence of bud | Young shoot | Dense | 7 | |
| 11 | Anthocyanin coloration at base of the patiole | Young shoot | Absent | 1 | |

TABLE 2-continued

Table of Characteristics: Kiyoka (data from two years; in cases where characteristic is identical in second year, per-year results are not shown).

| | | | | | |
|---|---|---|---|---|---|
| 12 | Length of "three and a bud" | Young shoot | Medium | 5 | 5.30 cm (2016) 4.94 cm (2017) |
| 13 | Time of plucking | | Early | 3 | Apr. 13, 2016 Apr. 20, 2017 |
| 14 | Number of buds at plucking time | Young shoot | Medium | 5 | 938 buds/$m^2$ (2016) 1206 buds/$m^2$ (2017) |
| 15 | Thickness of shoot | | Medium | 5 | 3.00 mm (2016) 3.29 mm (2017) |
| 16 | Leaf attitude | Mature leaf | Outwards | 3 | |
| 17 | Length of leaf blade | Mature leaf | Medium | 5 | 9.23 cm (2016) 9.68 cm (2017) |
| 18 | Width of leaf blade | Mature leaf | Medium | 5 | 3.49 cm (2016) 3.66 cm (2017) |
| 19 | Shape of leaf blade | Mature leaf | Medium elliptic | 3 | |
| 20 | Intensity of green color of leaf blade | Mature leaf | Light | 3 | 134A |
| 21 | Shape of cross section of leaf blade | Mature leaf | Flat | 2 | |
| 22 | Texture of upper surface of leaf blade | Mature leaf | Moderately rugose | 2 | |
| 23 | Shape of apex of leaf blade | Mature leaf | Acute | 2 | |
| 24 | Undulation of margin of leaf blade | Mature leaf | Absent or weak | 1 | |
| 25 | Serration of margin of leaf blade | Mature leaf | Medium | 5 | |
| 26 | Shape of base of leaf blade | Mature leaf | Actue | 1 | |
| 27 | Time of full flowering | Flower | Medium | 5 | Oct. 20, 2016 Oct. 28, 2017 |
| 28 | Length of pedicel | Flower | Medium | 5 | 10.2 mm (2016) 10.3 mm (2017) |
| 29 | Pubescence on outer side of sepal | Flower | Absent | 1 | |
| 30 | Anthocyanin coloration on sepal on outer side | Flower | Absent | 1 | |
| 31 | Diameter | Flower | Medium | 5 | 3.43 cm (2016) 3.44 cm (2017) |

TABLE 2-continued

Table of Characteristics: Kiyoka (data from two years; in cases where characteristic is identical in second year, per-year results are not shown).

| | | | | | |
|---|---|---|---|---|---|
| 32 | Color of innter | Flower | White (Upper & lower surface) | 2 | There is no appro-priate color on the RHS color chart. |
| 33 | Pubescence of ovary | Flower | Present | 9 | |
| 34 | Density of pubscence of ovary | Flower | Dense | 7 | |
| 35 | Length of style | Flower | Medium | 5 | 9.89 mm (2016) 10.29 mm (2017) |
| 36 | Position of style splitting | Flower | Medium | 5 | |
| 37 | Position of stigma | Flower | Same level | 3 | |
| 38 | Fermentation ability | | Medium | 5 | |
| 39 | Caffeine content | | Medium | 3 | 4.1% DW (2017) 4.5% DW (2018) |
| | Additional Characteristics | | | | |
| | Petiole length | | | | 4.13 mm (2020) |
| | Color of Petiole | | | | 141C |
| | Diameter of Flower Bud | | | | 7.51 mm |
| | Shape of Flower bud | | | | spherical shape |
| | Color of flower bud | | white | | There is no appro-priate color on the RHS color chart. |
| | Length of Sepal | | | | 4.25 mm |
| | Shape of Septal | | | | triangle with rounded edges |
| | Color of Sepal | | | | 134B |

| Charac-teris-tics | State/Score of reference variety | | | | | |
|---|---|---|---|---|---|---|
| | Yabukita | | | Saemidori | | |
| No. | state | score | data | state | score | data |
| 1 | Weak to medium | 4 | | Weak to medium | 4 | |
| 2 | Shrub | 1 | | Shrub | 1 | |
| 3 | upright to semi upright | 2 | | Semi upright | 3 | |
| 4 | Medium | 5 | | Dense | 7 | |
| 5 | Absent | 1 | | Absent | 1 | |

TABLE 2-continued

Table of Characteristics: Kiyoka (data from two years; in cases where characteristic is identical in second year, per-year results are not shown).

| | | | | | | |
|---|---|---|---|---|---|---|
| 6 | Medium | 5 | Mar. 27, 2016 Apr. 5, 2017 | Early | 3 | Mar. 19, 2016 Mar. 27, 2017 |
| 7 | Medium | 5 | Apr. 2, 2016 Apr. 10, 2017 | Early | 3 | Mar. 26, 2016 Apr. 5, 2017 |
| 8 | Medium green | 4 | 140A | Medium green | 4 | 140A |
| 9 | present | 9 | | present | 9 | |
| 10 | Medium | 5 | | Medium | 5 | |
| 11 | Absent | 1 | | Absent | 1 | |
| 12 | Medium | 5 | 5.43 cm (2016) 5.66 cm (2017) | Medium | 5 | 5.71 cm (2016) 4.49 cm (2017) |
| 13 | Medium | 5 | Apr. 22, 2016 Apr. 27, 2017 | Early | 3 | Apr. 14, 2016 Apr. 20, 2017 |
| 14 | Medium | 5 | 837 buds/$m^2$ (2016) 1238 buds/$m^2$ (2017) | Many | 7 | 1425 buds/$m^2$ (2016) 1662 buds/$m^2$ (2017) |
| 15 | Medium | 5 | 2.72 mm (2016) 2.93 mm (2017) | Medium | 5 | 2.78 mm (2016) 3.21 mm (2017) |
| 16 | Outwards | 3 | | Upwards to outwards | 2 | |
| 17 | Medium | 5 | 9.54 cm (2016) 9.18 cm (2017) | Medium | 5 | 8.99 cm (2016) 8.40 cm (2017) |
| 18 | Medium | 5 | 3.43 cm (2016) 3.53 cm (2017) | Medium | 5 | 3.15 cm (2016) 3.24 cm (2017) |
| 19 | Narrow elliptic | 2 | | Narrow elliptic | 2 | |
| 20 | Dark | 5 | 135B | Dark | 5 | 135B |
| 21 | Flat | 2 | | Flat | 2 | |
| 22 | Moderately rugose | 2 | | Moderately rugose | 2 | |
| 23 | Acute | 2 | | Acute | 2 | |
| 24 | Absent or weak | 1 | | Absent or weak | 1 | |
| 25 | Medium | 5 | | Medium | 5 | |
| 26 | Acute | 1 | | Acute | 1 | |
| 27 | Medium | 5 | Oct. 20, 2016 Oct. 28, 2017 | Medium | 5 | Oct. 18, 2016 Oct. 26, 2017 |
| 28 | Medium | 5 | 11.4 mm (2016) 11.2 mm (2017) | Medium | 5 | 10.7 mm (2016) 10.7 mm (2017) |
| 29 | Absent | 1 | | Absent | 1 | |
| 30 | Absent | 1 | | Absent | 1 | |
| 31 | Medium | 5 | 3.60 cm (2016) 3.42 cm (2017) | Medium | 5 | 3.49 cm (2016) 3.60 cm (2017) |
| 32 | White (Upper & lower surface) | 2 | There is no appro-priate color on the RHS color chart. | White (Upper & lower surface) | 2 | There is no appro-priate color on the RHS color chart. |

TABLE 2-continued

Table of Characteristics: Kiyoka (data from two years; in cases where characteristic is identical in second year, per-year results are not shown).

| | | | | | | |
|---|---|---|---|---|---|---|
| 33 | Present | 9 | | Present | 9 | |
| 34 | Dense | 7 | | Dense | 7 | |
| 35 | Low to medium | 4 | 9.33 mm (2016) 9.46 mm (2017) | Medium | 5 | 10.33 mm (2016) 10.00 mm (2017) |
| 36 | Medium | 5 | | Medium | 5 | |
| 37 | Same level | 3 | | Same level | 3 | |
| 38 | weak | 3 | | weak | 3 | |
| 39 | Medium | 3 | 3.5% DW (2017) 3.5% DW (2018) 4.24 mm (2020) 141C 7.06 mm spherical shape | Medium | 3 | 4.0% DW (2017) 3.9% DW (2018) 4.76 mm (2020) 141C 6.36 mm spherical shape |
| | white | | There is no appro-priate color on the RHS color chart. 4.33 mm triangle with rounded edges 134B | white | | There is no appro-priate color on the RHS color chart. 3.73 mm triangle with rounded edges 134B |

Data of Additional Characteristics were observed in Aug. 17, 2020.

Color scores are according to the Fifth Edition (2007) of "The Royal Horticultural Society (RHS) Color chart.

Currently, most green tea varieties that are prevalent in Japan are either the 'Yabukita' variety (accounting for approximately 75% of tea cultivation land area) or varieties whose aroma resembles 'Yabukita'. There is a lack of varieties having a strong unique aroma. Typically, for sencha, each tea company produces its own original sencha product by having a tea expert blend a number of varieties, with 'Yabukita' serving as the base. Tea varieties having a strong unique aroma of their own tend to ruin the balance between aroma and flavor when blended with 'Yabukita'. As such, there had previously been little demand for such varieties from commercial users. Currently, however, the needs of commercial users and consumers of tea are diversifying, and there is therefore a demand for new tea varieties which have their own strong, distinctive aroma. In recent times there has been an increase in development of tea products having new flavor/aroma by using existing varieties but modifying processing techniques to enhance the aroma. However, production methods for sencha normally use few varieties having their own strong, distinctive aroma. Furthermore, varieties that do have a characteristic aroma often have an astringent flavor. As such, the aim of the present tea variety is to breed a green tea variety which differs from conventional tea varieties by having a strong, distinctive aroma and excellent flavor.

Cross-breeding of 'Kiyoka' was carried out in 1998 at Makurazaki-shi in Kagoshima, Japan. Seed collection, sowing, and cultivation was performed in 1999. In 1998, an F1 seedling group was obtained by crossbreeding (i) FYZ-41 (seed parent), which has a strong floral fragrance, and (ii) 'Saemidori' (pollen parent), which is early maturing and provides excellent processed tea quality. 'FYZ-41' is a line that has not been established as a variety. In breeding tea, such a line may be used as a hybrid parent in cases where specific characteristic data concerning the line is not completely available but the line only has target characteristics. 'FYZ-41' was used as a female parent because it had the target characteristic scent of flowers, however specific characteristic data concerning 'FYZ-41' is not available. 'Kiyoka' was selected from this F1 seedling group in an individual selection test in 2005 (see FIG. 1). Individual selection tests were performed from 2001 to 2005. Thereafter, 'Kiyoka' was submitted under the name 'Makurazaki 54-20' to clonal line comparison test group 54, and was found to have an excellent distinctive aroma. In 2005, propagation by cutting (nursery selection) was performed. Clonal line comparison testing took place from 2006 to 2012. Local adaptability testing, as well as testing for specific characteristics, was performed from 2011 to 2018. In 2011, 'Kiyoka' was submitted under the name 'Yachaken 04 Gou' to local adaptability test group No. 13. Furthermore, in 2014, 'Kiyoka' was subjected to cultivation and processing testing as a candidate variety having excellent color and flavor/aroma in a "science and technology research promotion program for agriculture, forestry, fisheries and food industry" (plant variety producing project), specifically a program for "breeding of tea variety suited for commercial user needs, and development of techniques for cultivation, processing, and use thereof".

Morphological Characteristic

Plant growth habit is semi upright to spreading. Plant vigor is medium to strong. Plant is of "gajugata" (bud weight) type. Cutting propagation rate is favorable. Data from 2017 local adaptability tests shows plant spread to be somewhat larger than 'Yabukita', and somewhat smaller than 'Saemidori', and therefore nearly the equivalent to that of parent strains 'Yabukita' and 'Saemidori'. The fruit and seed of 'Kiyoka' take a form similar to that taken by the fruit and seed of a common tea tree. Specifically, the fruit is capsular, and most of the fruit is occupied by seed(s). The fruit includes several seeds (ordinarily 1 seed to 3 seeds) that are enclosed by the pericarp and each of which is a grain including the embryo and albumen that are enclosed by a seed coat.

In local adaptability tests, the average for fresh leaf yield of 'Kiyoka' was, for first flush, less than that of 'Yabukita' and 'Saemidori', and for the second flush, was equivalent to that of 'Yabukita' and less than that of 'Saemidori'. At the breeding site, yield across all tea-plucking seasons (first flush to third flush) was less than that of 'Saemidori', but greater than that of 'Yabukita'. 'Kiyoka' also exhibits excellent color, with dark green fresh leaves. SPAD value (an index of chlorophyll content) was higher than in 'Yabukita' and equivalent to or higher than in 'Saemidori' in all tea-plucking seasons.

Additional properties and characteristics of 'Kiyoka', which may serve as useful reference in variety examination, are described in Table 3.

TABLE 3

Additional properties and characteristics of 'Kiyoka'.

| Denomination of Similar Variety | Description of Characteristics | State of Expression in Similar Variety | State of Expression in 'Kiyoka' |
|---|---|---|---|
| Yabukita | Blister blight resistance | Weak to medium | Medium to strong |
| Yabukita | Gray blight resistance | Weak | Medium |
| Saemidori | Gray blight resistance | Weak | Medium |
| Saemidori | Anthracnose resistance | Medium | Weak to medium |

Ecological Characteristics

'Kiyoka' was found to be early budding, with the time of first flush sprouting in Japan being 13 days earlier than for 'Yabukita', and time of plucking in Japan being 8 days earlier than for 'Yabukita'. In the local adaptability tests, average data (year-on-year cumulative average) showed 'Kiyoka' time of sprouting being 4 days earlier than for 'Yabukita' and time of plucking being 2 days earlier than for Yabukita.

The field resistance of 'Kiyoka' to natural occurrence of anthracnose in autumn was deemed to be "weak to medium". In inoculation tests, resistance to anthracnose was similarly found to be "weak to medium". As such, 'Kiyoka' was deemed to have anthracnose resistance which is, overall, "weak to medium". Gray blight (*Discula theae-sinensis*) resistance was "medium". Resistance against both anthracnose and gray blight was slightly stronger than in 'Yabukita'. Resistance to bacterial shoot blight in field inoculation tests was found to be "weak". Blister blight resistance was determined to be "medium to strong" in tests for specific characteristics. Resistance to white peach scale (*Pseudaulacaspis pentagona*) was determined to be "weak", with degree of occurrence being equivalent to that of Yabukita.

'Kiyoka' was examined for natural occurrence of anthracnose in the local adaptability tests. It was found that, although the score for degree of occurrence differed between regions, the average score was 2.7, with a maximum of 5.0. This score represented a lower degree of occurrence than in 'Yabukita' (3.4), but higher than in 'Saemidori' (2.5). At the breeding site, an inoculation test and in-field natural occurrence test for anthracnose were carried out. Comprehensively considering the data from both the local adaptability tests and from the breeding site, resistance against anthracnose is deemed to be "weak to medium".

'Kiyoka' was examined for natural occurrence of gray blight in the older version of the local adaptability tests. It was found that the average score for occurrence degree was 1.2, which was less than the average for 'Yabukita' (1.7). Furthermore, in an inoculation test at the breeding site, 'Kiyoka' was determined to have medium resistance against gray blight. As such, 'Kiyoka' is deemed to have practical resistance against gray blight, and fungicide spraying is therefore unnecessary.

In the local adaptability tests, occurrence of bacterial shoot blight (*Pseudomonas syringae* pv. *theae*) in 'Kiyoka' was observed only in Shizuoka Prefecture in Japan. At Shizuoka, the degree of occurrence was higher than in both 'Yabukita' and 'Saemidori'. An in-field inoculation test for bacterial shoot blight was carried out at the breeding site, and it was found that for 'Kiyoka', the number of symptomatic leaves was less compared to 'Yabukita', but somewhat more compared to 'Saemidori'. In 2015 research data by the NARO Institute of Vegetable and Tea Science, 'Yabukita' and 'Saemidori' were determined to have weak resistance against bacterial shoot blight. In view of this data, 'Kiyoka' was also determined to have weak resistance against bacterial shoot blight.

A field resistant test for blister blight (*Exobasidium vexans*) was carried out in Shizuoka Prefecture in Japan. It was found that in 'Kiyoka', the degree of blister blight occurrence was consistently lower than that of the comparative variety 'Okuhikari', and thus 'Kiyoka' was deemed to have medium to strong resistance.

In the older version of the local adaptability tests, the average score for occurrence of *Pseudaulacaspis pentagona* was 3.4, with a maximum score of 5.0. The degree of occurrence in 'Kiyoka' was equivalent to that of 'Yabukita' and 'Saemidori', which are both considered to have weak resistance. 'Kiyoka' resistance to Pseudaulacaspis pentagona was therefore determined to be weak.

With regard to the resistance of 'Kiyoka' to cold, resistance to cold injury in winter leaves (wilting in which leaves turn reddish-brown due to cold temperatures) was found to be "medium to weak", which is lower than that of 'Yabukita' but equivalent to that of 'Saemidori'. Resistance to bark splitting frost damage was "medium," which is equivalent to that of Yabukita.

In the older version of the local adaptability tests, the 'Kiyoka' scores for cold injury in winter leaves had a maximum value of 5.0 in Japan, indicating greater damage than in 'Yabukita' (4.0). In a cold injury resistance test at the breeding site, 'Kiyoka' was determined to have weak to medium resistance, which is equivalent to the rating for 'Saemidori', but lower than Yabukita's resistance (2017 research data by the National Agriculture and Food Research Organization).

A cold drought damage of winter leaves is wilting in which leaves wilt due to lack of moisture; leaves maintain a green color but lose gloss. In local adaptability tests, cold drought damage was observed only in Saitama Prefecture in Japan. The score for degree of occurrence of cold drought damage was 5.0 for 'Kiyoka', which was equivalent to the score for 'Yabukita'. As such, there is the risk that cold drought damage will occur in colder regions having a yearly average temperature of 9 to 12 degrees Celsius.

A test for specific characteristics regarding resistance to bark splitting frost damage was carried out in Kagoshima Prefecture in Japan. As a result, 'Kiyoka' was found to have medium resistance, which was equivalent to the rating for 'Yabukita'.

Quality Characteristics and Processability

In standard cultivation, 'Kiyoka' is an early budding variety for use as sencha (a type of Japanese green tea which is prepared by infusing the processed whole tea leaves in hot water). Suitable cultivation sites for 'Kiyoka' are warm regions having a yearly average temperature of 15 to 18 degrees Celsius. When permanently planting 'Kiyoka' in moderately warm regions having a yearly average temperature of 12 to 15 degrees Celsius, it is necessary to carefully determine the weather conditions of the tea field, including choosing a location with sufficient sunlight and little frost.

Because 'Kiyoka' is an early budding variety, it is necessary to implement anti-frost measures in regions where late frost damage can occur. Anthracnose occurrence is less prevalent than in 'Yabukita', but it is preferable to implement fungicide control measures. Pesticide spraying against bacterial shoot blight are necessary in regions where occurrence of bacterial shoot blight is observed.

In local adaptability tests, the average for first flush processed tea quality of 'Kiyoka' was equivalent to that of 'Yabukita', and lower than that of 'Saemidori'. The average for second flush processed tea quality was somewhat better than that of both 'Yabukita' and 'Saemidori'. This is presumably because the aroma and flavor of 'Kiyoka' have a floral fragrance unique to the variety, and thus when 'Kiyoka' was tested as sencha, depending on the test location, it was deemed to have flavor and aroma which were of a different nature to sencha. Note that at the breeding site, 'Kiyoka' was found to have processed tea quality which exceeded that of both 'Saemidori' and 'Yabukita' in all tea-plucking seasons, and was found to have a distinctive floral fragrance.

Plant Growth

Cultivation characteristics, processed tea quality, and chemical composition were examined for 'Kiyoka' and 'Sofu', which is an existing early budding variety that has an oriental-orchid-like floral fragrance. The two varieties are similar in terms of plant growth habit, plant vigor, time of sprouting, and date of plucking, but 'Kiyoka' has a higher fresh leaf yield and higher number of buds per square meter. Upon evaluation of SPAD value (which indicates chlorophyll content), it was found that Sofu had a higher SPAD value at first flush, whereas 'Kiyoka' had a higher SPAD value at second flush. However, regarding processed tea quality, it was found that 'Kiyoka' had superior color of processed tea at both first flush and second flush. 'Kiyoka' had superior processed tea quality at both first flush and second flush, with an aroma having a strong, distinctive floral fragrance, and a superior flavor as well. In a comparison of chemical composition, it was found that at both first flush and second flush, 'Kiyoka' had a higher total nitrogen and free amino acid content than Sofu, and an equivalent tannin content and caffeine content. It is presumed that the higher free amino acid content is reflected in the difference in flavor. Thus, these results indicate that 'Kiyoka' is superior to Sofu in terms of both yield and processed tea quality.

In the local adaptability tests, regarding the chemical composition of 'Kiyoka' across all tea-plucking seasons, total nitrogen content and free amino acid content was higher than in 'Yabukita' in some test sites, but somewhat lower than 'Saemidori'. Tannin content was equivalent to or slightly lower than in 'Yabukita', and slightly higher than in 'Saemidori'. At the breeding site, across all tea-plucking seasons, total nitrogen content and free amino acid content in 'Kiyoka' was higher than in 'Yabukita', and nearly equivalent to that of 'Saemidori'.

Other Characteristics

At the breeding site, during all tea-plucking seasons (first flush through third flush), yield of 'Kiyoka' was greater than that of 'Yabukita' and somewhat less than that of 'Saemidori'. In all tea-plucking seasons (first flush through third flush), processed tea quality was superior to that of 'Saemidori', which is a high-quality variety. The aroma of 'Kiyoka' was found to have a distinctive floral fragrance. In the local adaptability tests, average values for both first flush yield and second flush yield of 'Kiyoka' were less than those of 'Saemidori'. First flush yield was less than that of 'Yabukita', but second flush yield was greater than that of 'Yabukita'. The average values for processed tea quality of both first flush and second flush of 'Kiyoka' were equivalent to those for 'Yabukita', and slightly lower than those for 'Saemidori'.

'Kiyoka' was grown in open culture. In Japan, planting occurs in early February to early April. In Japan cutting time is early June to late June. In Japan, flowering occurs in early October to mid-November, and harvesting time is early April to mid-April.

It will be understood that the average size of the plant and tea quality may vary with location, season, nutrition, irrigation, etc.

What is claimed is:

1. A new and distinct *Camellia sinensis* (L.) Kuntze plant named 'Kiyoka' as illustrated and described herein.

* * * * *